(12) United States Patent
Ma et al.

(10) Patent No.: US 11,653,982 B2
(45) Date of Patent: May 23, 2023

(54) OSTEOTOMY CALIBRATION METHOD, CALIBRATION TOOLS AND ORTHOPEDIC SURGERY SYSTEM

(71) Applicant: Suzhou MicroPort Orthobot Co., Ltd., Jiangsu (CN)

(72) Inventors: Jingyang Ma, Jiangsu (CN); Feng Sun, Jiangsu (CN); Hui Shao, Jiangsu (CN); Chao He, Jiangsu (CN); Pengfei Liu, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 427 days.

(21) Appl. No.: 16/849,146

(22) Filed: Apr. 15, 2020

(65) Prior Publication Data
US 2021/0153951 A1 May 27, 2021

(30) Foreign Application Priority Data
Nov. 21, 2019 (CN) .......................... 201911151229.4

(51) Int. Cl.
*A61B 34/20* (2016.01)
*A61B 34/30* (2016.01)
(Continued)

(52) U.S. Cl.
CPC ............ *A61B 34/20* (2016.02); *A61B 17/151* (2013.01); *A61B 34/30* (2016.02); *A61B 90/39* (2016.02);
(Continued)

(58) Field of Classification Search
CPC combination set(s) only.
See application file for complete search history.

(56) References Cited

U.S. PATENT DOCUMENTS

| 8,483,434 B2 | 7/2013 | Buehner et al. |
| 10,034,711 B2 | 7/2018 | Greenwald et al. |

(Continued)

FOREIGN PATENT DOCUMENTS

| CN | 101426453 A | 5/2009 |
| CN | 102258399 A | 11/2011 |

(Continued)

*Primary Examiner* — Sameh R Boles
(74) *Attorney, Agent, or Firm* — Muncy, Geissler, Olds & Lowe, P.C.

(57) ABSTRACT

An osteotomy calibration method, calibration tools, a readable storage medium, and an orthopedic surgery system are provided. Firstly using the plane calibration tool to obtain the calculated position information of the current osteotomy plane, and then determining a position error between the calculated position information and a predetermined position information of a planned osteotomy plane, and if the position error exceeds a preset value, calculating and transmitting a relocation information to a robotic arm to control and relocate the robotic arm. By comparing and identifying the position error between the current osteotomy plane formed by the first osteotomy and the planned predetermined osteotomy plane, relocating the robotic arm, and performing a secondary correction of the osteotomy plane. In addition, by relocating the robotic arm and secondary correction of the osteotomy plane, additional bone nails which is to fix the navigation tool to the bone can be avoided.

6 Claims, 10 Drawing Sheets

(51) Int. Cl.
*A61B 90/00* (2016.01)
*A61B 17/15* (2006.01)
(52) U.S. Cl.
CPC ............... *A61B 2034/2055* (2016.02); *A61B 2090/3983* (2016.02)

(56) References Cited

U.S. PATENT DOCUMENTS

| | | | |
|---|---|---|---|
| 10,702,343 B2 * | 7/2020 | Kozak | ............... A61B 17/7083 |
| 2008/0319491 A1 | 12/2008 | Schoenefeld | |
| 2014/0206990 A1 | 7/2014 | Epstein et al. | |
| 2019/0053852 A1 | 2/2019 | Schoenefeld | |

FOREIGN PATENT DOCUMENTS

| | | |
|---|---|---|
| CN | 105813592 A | 7/2016 |
| CN | 107468350 A | 12/2017 |
| CN | 107920860 A | 4/2018 |
| CN | 108294825 A | 7/2018 |
| CN | 109171962 A | 1/2019 |
| CN | 109925055 A | 6/2019 |
| CN | 110114019 A | 8/2019 |
| EP | 3569159 A1 | 11/2019 |
| WO | WO2016154548 A1 | 9/2016 |
| WO | WO-2018104523 A1 | 6/2018 |
| WO | WO2019128961 A1 | 7/2019 |

* cited by examiner

OSTEOTOMY CALIBRATION METHOD, CALIBRATION TOOLS AND ORTHOPEDIC SURGERY SYSTEM

CROSS-REFERENCE TO RELATED APPLICATION

This application claims the priority of Chinese patent application number 201911151229.4, filed on Nov. 21, 2019, the entire contents of which are incorporated herein by reference.

TECHNICAL FIELD

The present application relates to the field of robot-assisted surgery system and method, and in particular, to an osteotomy calibration method, calibration tools, a readable storage medium, and an orthopedic surgery system.

BACKGROUND

In an artificial joint replacement surgery, a variety of positioners, navigation devices and the like are needed for osteotomy before installation of the artificial joint so that the accuracy of the osteotomy operation could be ensured. Different methods have been proposed to help surgeons achieve the positioning of osteotomy navigation tools during total knee arthroplasty (TKA) surgery. Generally, in the existing robot-assisted surgery system, an osteotomy tool is arranged at the end of the robotic arm, and the movement of the osteotomy tool is controlled by the robotic arm to realize the positioning of the osteotomy tool during knee arthroplasty surgery. However, the accuracy is determined by the absolute positioning accuracy of the robotic arm, and the osteotomy surface cannot be tracked and calibrated during osteotomy, which affects the accuracy of the operation. In addition, during osteotomy, the saw blade swings in a direction perpendicular to the saw blade due to the force, which may easily cause an error between the planned osteotomy position and the actual osteotomy position.

SUMMARY OF THE INVENTION

An object of the present application is to provide an osteotomy calibration method, calibration tools, a readable storage medium, and an orthopedic surgery system so as to solve the problem of low accuracy of the existing osteotomy.

To solve the above technical problems, according to a first aspect of the present application, there is provided an osteotomy calibration method, including:

calculating a position information of a detection plane of a plane calibration tool placed on a current osteotomy plane, and defining the position information of the detection plane as a calculated position information of the current osteotomy plane;

determining a position error between the calculated position information and a predetermined position information based on a planned osteotomy plane, and if the position error exceeds a preset value, calculating and transmitting a relocation information to a robotic arm so as to control and relocate the robotic arm.

Optionally, in the osteotomy calibration method, the calculated position information includes a calculating normal vector and a calculated position, and wherein the position error includes:

a normal vector rotation matrix of the calculating normal vector and a predetermined normal vector based on the predetermined normal vector and the predetermined position of the planned osteotomy plane; and a position deviation between the calculated position and the predetermined position of the planned osteotomy plane.

Optionally, in the osteotomy calibration method, if at least one of the normal vector rotation matrix and the position deviation exceeds a preset value, the robotic arm relocates according to the normal vector rotation matrix and the position deviation.

Optionally, in the osteotomy calibration method, the detection plane is provided with a trackable element, and wherein the step of calculating the position information of the detection plane includes:

determining a calculating normal vector $\vec{n}_V$ and a calculated position $P_V(x_V, y_V, z_V)$ of the detection plane in a lower limb DICOM data coordinate system based on a normal vector $\vec{n}_P$ and a position $P_P(x_P, y_P, z_P)$ of the detection plane in a trackable element coordinate system of the plane calibration tool, and a transformation matrix $M_{P \to V}$ between the trackable element coordinate system and the lower limb DICOM data coordinate system.

Optionally, in the osteotomy calibration method, the plane calibration tool includes two or more detection planes to check two or more current osteotomy planes, wherein at least one of the detection planes is provided with a trackable element and is defined as a first detection plane, and one or more detection planes adjacent to the first detection plane are defined as second detection planes, and wherein calculating the position information of the detection plane includes:

calculating a position information of the first detection plane;

acquiring a first angle between the first detection plane and the second detection plane adjacent to the first detection plane;

calculating a position information of the second detection plane according to the first angle.

Optionally, in the osteotomy calibration method, a distance between the second detection plane and the trackable element of the first detection plane is adjustable, and wherein the step of calculating the position information of the detection plane further includes:

acquiring a displacement of the second detection plane with respect to the trackable element; and calculating the position information of the second detection plane according to the angle and the displacement.

Optionally, in the osteotomy calibration method, the plane calibration tool includes a third detection plane, wherein a first side of the third detection plane and the first detection plane are spaced apart by at least one of the second detection planes; and wherein the step of calculating the position information of the detection plane includes:

acquiring a position information of one of the detection planes adjacent to the first side of the third detection plane;

acquiring a second angle between the third detection plane and the one of the detection planes adjacent to the first side of the third detection plane;

acquiring a displacement of the third detection plane with respect to another one of the detection planes located at the first side and indirectly adjacent to the third detection plane;

calculating a position information of the third detection plane according to the second angle and the displacement.

Optionally, in the osteotomy calibration method, the detection plane is provided with a trackable element, and wherein the osteotomy calibration method includes: calibrating a relative position of the detection plane with respect to the trackable element.

Optionally, in the osteotomy calibration method, comprising:

calibrating a plurality of marked points on the detection plane by using a trackable tool with tips;

obtaining coordinates of the plurality of marked points in a reflective spherical coordinate system of the trackable tool;

calculating a real position and a real normal vector of the detection plane; and comparing the real position and the real normal vector with original data so as to detect whether the plane calibration tool is deformed.

To solve the above technical problems, according to a second aspect of the invention, there is provided a plane calibration tool, comprising at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking.

Optionally, in the plane calibration tool, the plan calibration tool includes two or more detection planes, and each of the detection planes is provided with a trackable element, wherein the two or more detection planes are rotatably connected in sequence, and if the detection planes are more than two, a length of at least a middle one of the detection planes is adjustable.

Optionally, in the plane calibration tool, the plan calibration tool includes two or more detection planes rotatably connected in sequence, wherein at least one of the detection planes is provided with the trackable element and is defined as a first detection plane, and one or more detection planes adjacent to the first detection plane are defined as second detection planes, wherein a distance between the trackable element of the first detection plane and an adjacent one of the second detection planes is fixed, and wherein an angle sensor is arranged therebetween and configured to sense an angle between the first detection plane and the adjacent one of the second detection planes.

Optionally, in the plane calibration tool, the plane calibration tool includes three or more detection planes rotatably connected in sequence, and wherein a length of at least a middle one of the detection planes is adjustable.

Optionally, in the plane calibration tool, wherein the plane calibration tool includes at least one third detection plane, and the third detection plane has a first side and a second side opposite to the first side, wherein the first side of the third detection plane and the first detection plane are spaced apart by at least one second detection plane, wherein an angle sensor is arranged between the third detection plane and one of the detection planes adjacent to the first side of the third detection plane, and wherein a displacement sensor is arranged on the one of the detection plane adjacent to the first side of the third detection plane, and the displacement sensor is configured to sense a displacement of the third detection plane with respect to another one of the detection planes located at the first side and indirectly adjacent to the third detection plane.

Optionally, in the plane calibration tool, wherein the plan calibration tool includes two or more detection planes rotatably connected in sequence, wherein at least one of the detection planes is provided with the trackable element and is defined as a first detection plane, and one or more detection planes adjacent to the first detection plane are defined as second detection planes, wherein the distance between the trackable element of the first detection plane and an adjacent one of the second detection planes is adjustable, and wherein a displacement sensor is provided on the first detection plane, and the displacement sensor is configured to sense a displacement of the second detection plane relative to the trackable element.

Optionally, in the plane calibration tool, wherein the plane calibration tool includes at least one third detection plane, and the third detection plane has a first side and a second side opposite to the first side, wherein the first side of the third detection plane and the first detection plane are spaced apart by at least one second detection plane, wherein an angle sensor is arranged between the third detection plane and one of the detection planes adjacent to the first side of the third detection plane, and wherein a displacement sensor is arranged on the one of the detection plane adjacent to the first side of the third detection plane, and the displacement sensor is configured to sense a displacement of the third detection plane with respect to another one of the detection planes located at the first side and indirectly adjacent to the third detection plane. To solve the above technical problems, according to a third aspect of the present application, there is provided an orthopedic surgery system which includes: a control device, a navigation device, a robotic arm, and a plane calibration tool, wherein the plane calibration tool comprises at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking;

wherein the navigation device matches with the plane calibration tool so as to obtain a position information of the trackable element and feedback the position information to the control device; and wherein the control device is configured to obtain a calculated position information of a current osteotomy plane according to the position information of the trackable element of the plane calibration tool, and to determine a position error between the calculated position information and a predetermined position information of a planned osteotomy plane, and if the position error exceeds a preset value, the control device drives and relocates the robotic arm.

Optionally, in the orthopedic surgery system, wherein the plan calibration tool includes two or more detection planes, and each of the detection planes is provided with a trackable element, wherein the two or more detection planes are rotatably connected in sequence, and if the detection planes are more than two, a length of at least a middle one of the detection planes is adjustable.

In the orthopedic surgery system, wherein the plan calibration tool includes two or more detection planes rotatably connected in sequence, wherein at least one of the detection planes is provided with the trackable element and is defined as a first detection plane, and one or more detection planes adjacent to the first detection plane are defined as second detection planes, wherein: a distance between the trackable element of the first detection plane and an adjacent one of the second detection planes is fixed, and an angle sensor is arranged therebetween and configured to sense an angle between the first detection plane and the adjacent one of the second detection planes.

In the orthopedic surgery system, wherein the plan calibration tool includes two or more detection planes rotatably connected in sequence, wherein at least one of the detection planes is provided with the trackable element and is defined as a first detection plane, and one or more detection planes adjacent to the first detection plane are defined as second detection planes, wherein: a distance between the trackable element of the first detection plane and an adjacent one of the second detection planes is adjustable, and a displacement sensor is provided on the first detection plane, and the displacement sensor is configured to sense a displacement of the second detection plane relative to the trackable element.

In summary, in an osteotomy calibration method, calibration tools, a readable storage medium, and an orthopedic surgery system provided by the present application, firstly using the plane calibration tool to obtain the calculated position information of the current osteotomy plane, and then determining a position error between the calculated position information and a predetermined position information of a planned osteotomy plane, and if the position error exceeds a preset value, calculating and transmitting a relocation information to a robotic arm so as to control and relocate the robotic arm. In this way, by comparing and identifying the position error between the current osteotomy plane formed by the first osteotomy and the planned predetermined osteotomy plane, relocating the robotic arm, and performing a secondary correction of the osteotomy plane, which can improve the final accuracy of the osteotomy plane. In addition, by relocating the robotic arm and secondary correction of the osteotomy plane, additional bone nails which is to fix the navigation tool to the bone can be avoided. Therefore, the patient's trauma surface and surgical time can be reduced.

BRIEF DESCRIPTION OF THE DRAWINGS

Those of ordinary skill in the art will understand that the accompanying drawings are provided for better understanding of the present application, and do not limit the scope of the present application in any way, in which.

Figure 1:
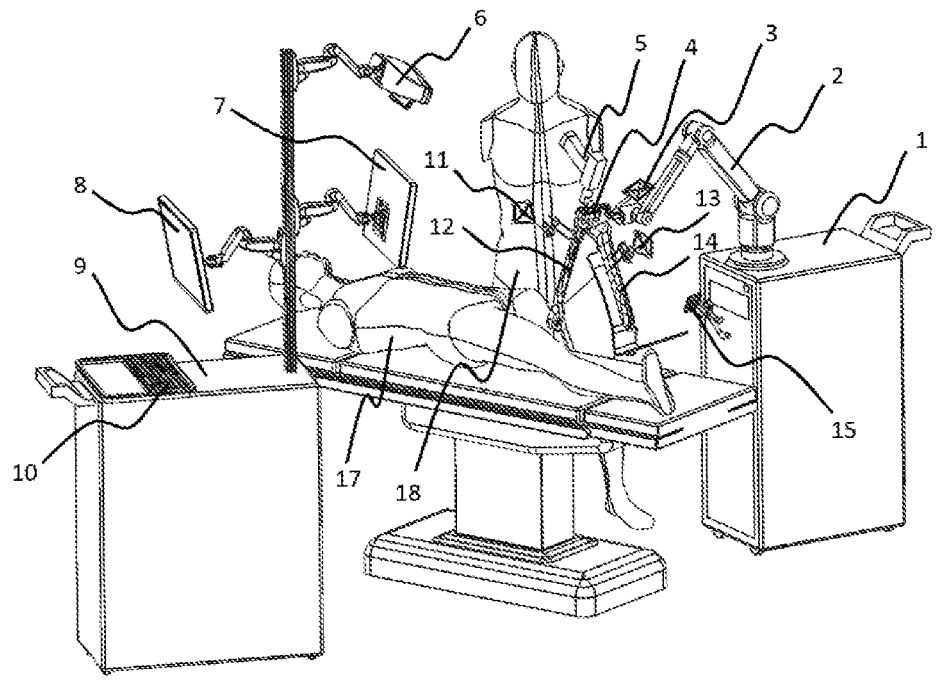
FIG. 1 is a schematic diagram of knee arthroplasty by using orthopedic surgery system according to Embodiment 1 of the present application.

In these drawings:
1: a surgical trolley; 2: a robotic arm; 3: a tool trackable element; 4: an osteotomy navigation tool; 5: a pendulum saw; 6: an NDI navigation device; 7: an auxiliary display; 8: a main display; 9: a navigation trolley; 10: a keyboard; 11: a femoral trackable element; 12: a femur; 13: a tibia trackable element; 14: a tibia; 15: a base trackable element; 17: a patient; 18: an operator;
111: a first detection plane; 111: a marked point; 112: a second detection plane; 113: a third detection plane; 113: a first side; 113b: a second side; 114: an angle sensor; 115: a displacement sensor; 116: a telescopic section; 117: a fixed section; 200: a trackable element; 201: a reflection sphere; 202: a magnetic coil; 203: a SIU module.

DETAILED DESCRIPTION

Features and advantages of the invention will be more apparent from the following detailed description. It is noted that the figures are provided in a very simplified form and not necessarily drawn to scale, with the only intention to facilitate convenience and clarity in explaining the embodiment. In addition, the structures shown in the drawings are often a part of the actual structure. In particular, different emphasis of the drawings is needed to be shown, and sometimes different scales are used.

As used in the present application, the singular forms "a," "an," and "the" include plural referents unless otherwise specified in the content. As used in the present application, the term "or" is generally used in a meaning including "and/or" unless otherwise specified in the content. As used in the present application, the term "multiple" is generally used in a meaning including "at least one" unless otherwise specified in the content. As used in the present application, the term "at least two" is generally used in a meaning including "two or more" unless otherwise specified in the content. In addition, the terms "first", "second", and "third" are used for descriptive purposes only, and cannot be understood as indicating or implying relative importance or implicitly indicating the number of technical features indicated. Therefore, the features defined as "first", "second", and "third" may explicitly or implicitly include one or at least two of the features.

The core idea of the present application is to provide to an osteotomy calibration method, calibration tools, a readable storage medium, and an orthopedic surgery system to solve the problem of low accuracy of the existing osteotomy.

The osteotomy calibration method comprises: calculating a position information of a detection plane of a plane calibration tool placed on a current osteotomy plane, and defining the position information of the detection plane as a calculated position information of the current osteotomy plane; determining a position error between the calculated position information and a predetermined position information based on a planned osteotomy plane, and if the position error exceeds a preset value, calculating and transmitting a relocation information to a robotic arm so as to control and relocate the robotic arm.

The plane calibration tool includes at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking.

The readable storage medium has a program stored thereon, and when the program is executed, the program is implemented according to the osteotomy calibration method as described above.

The orthopedic surgery system comprising a control device, a navigation device, a robotic arm, and a plane calibration tool, wherein the plane calibration tool comprises at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking; wherein the navigation device matches with the plane calibration tool so as to obtain a position information of the trackable element and feedback the position information to the control device; and wherein the control device is configured to obtain a calculated position information of a current osteotomy plane according to the position information of the trackable element of the plane calibration tool, and to determine a position error between the calculated position information and a predetermined position information of a planned osteotomy plane, and if the position error exceeds a preset value, the control device drives and relocates the robotic arm.

In this way, by comparing and identifying the position error between the current osteotomy plane formed by the first osteotomy and the planned predetermined osteotomy plane, the robotic arm is relocated, and then the osteotomy plane is performed by a further or secondary correction, which can improve the final accuracy of the osteotomy plane. In addition, by relocating the robotic arm and performing the secondary correction of the osteotomy plane, additional bone nail which is used to fix the navigation tool to the bone can be avoided. Therefore, the patient's trauma surface and surgical time can be reduced.

The following description is made with reference to the drawings.

Embodiment 1

Figure 2:
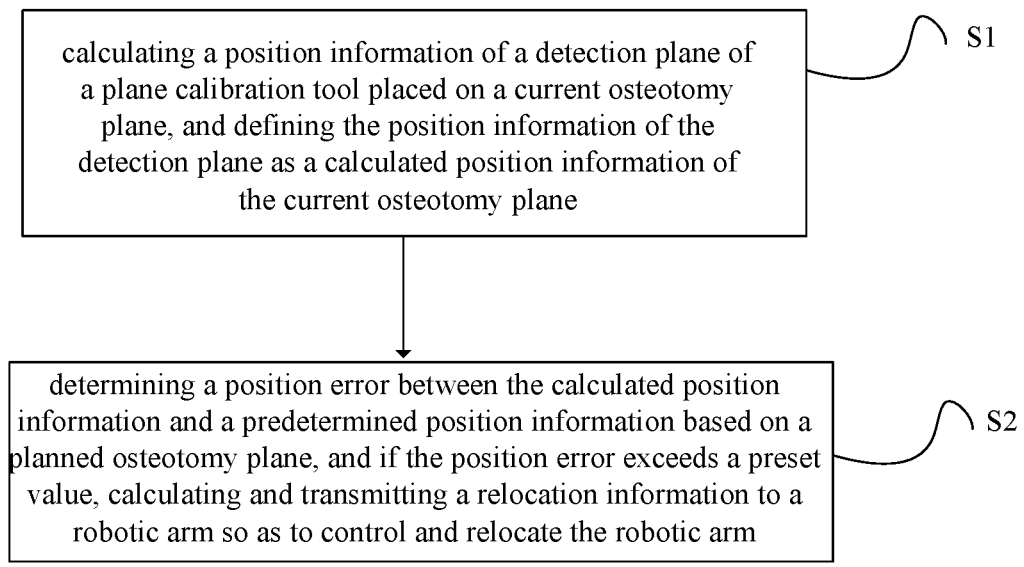
FIG. 2 is a flowchart of an osteotomy calibration method according to Embodiment 1 of the present application.
Figure 3:
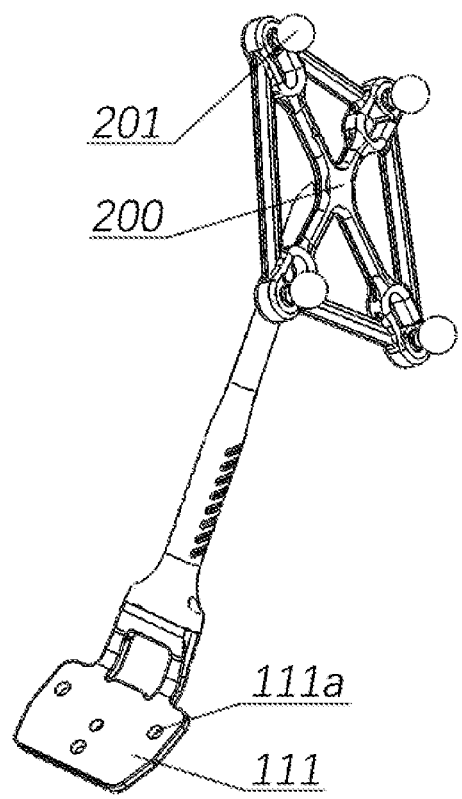
FIG. 3 is a schematic diagram of a plane calibration tool according to a first example of Embodiment 1 of the present application.
Figure 4:
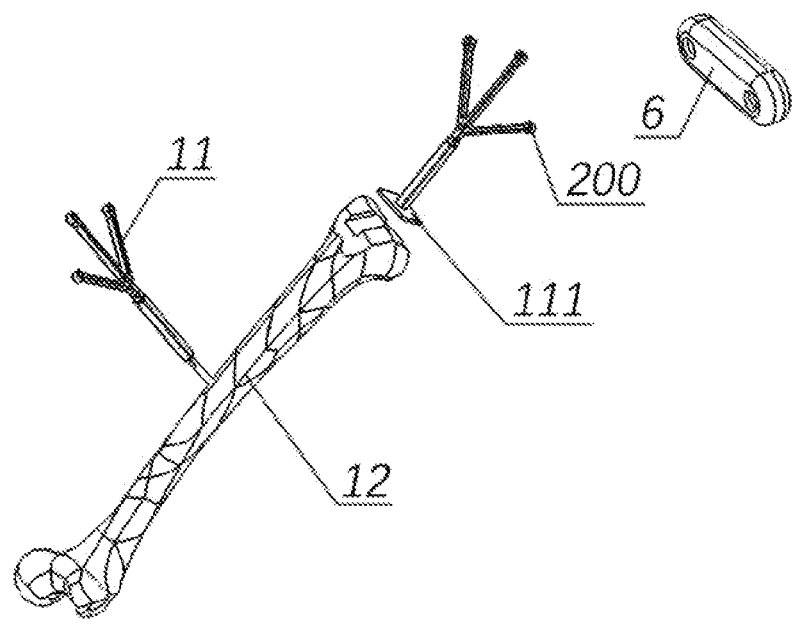
FIG. 4 is a schematic diagram of usage of a plane calibration tool according to a first example of Embodiment 1 of the present application.
Figure 5:
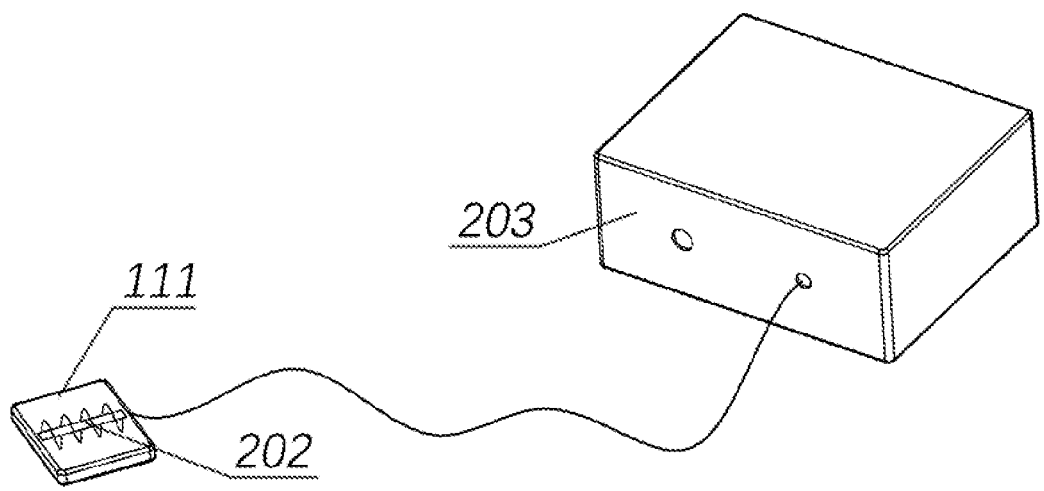
FIG. 5 is a schematic diagram of a plane calibration tool according to a second example of Embodiment 1 of the present application.
Figure 6:
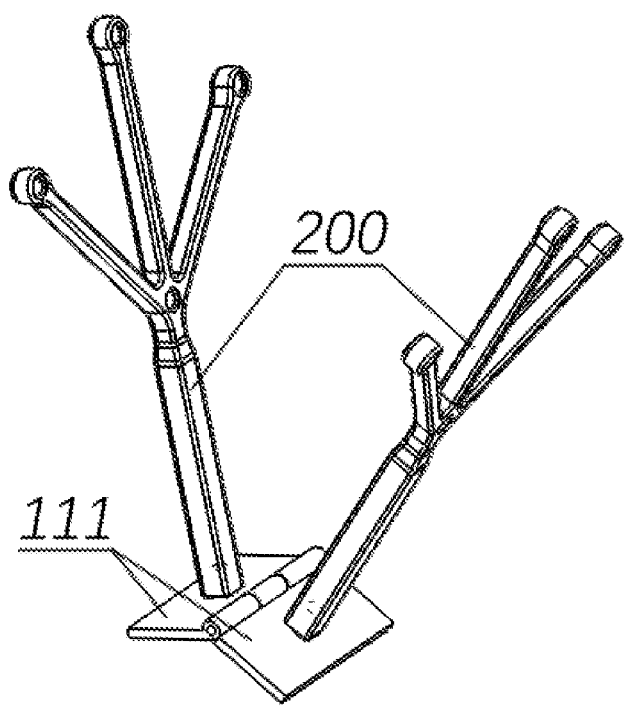
FIG. 6 is a schematic diagram of a plane calibration tool according to a third example of Embodiment 1 of the present application.
Figure 7:
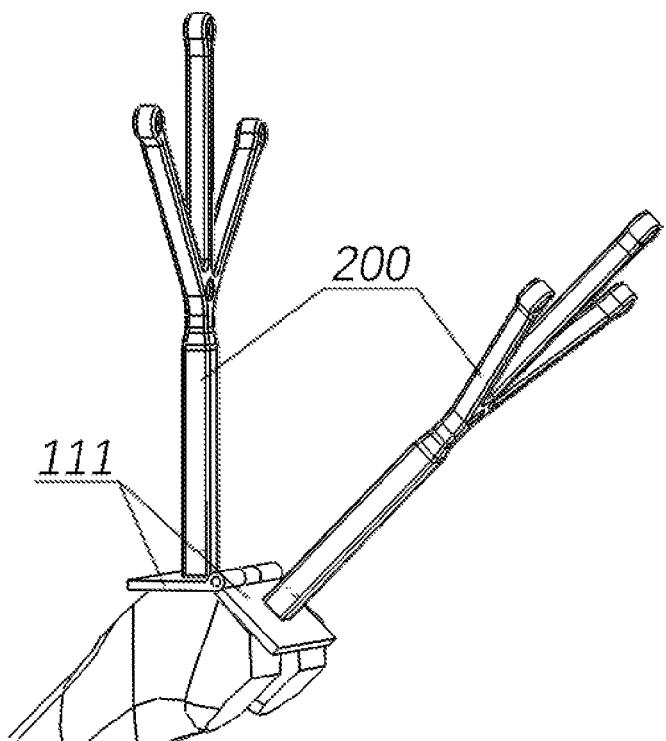
FIG. 7 is a schematic diagram of usage of a plane calibration tool according to a third example of Embodiment 1 of the present application.
Figure 8:
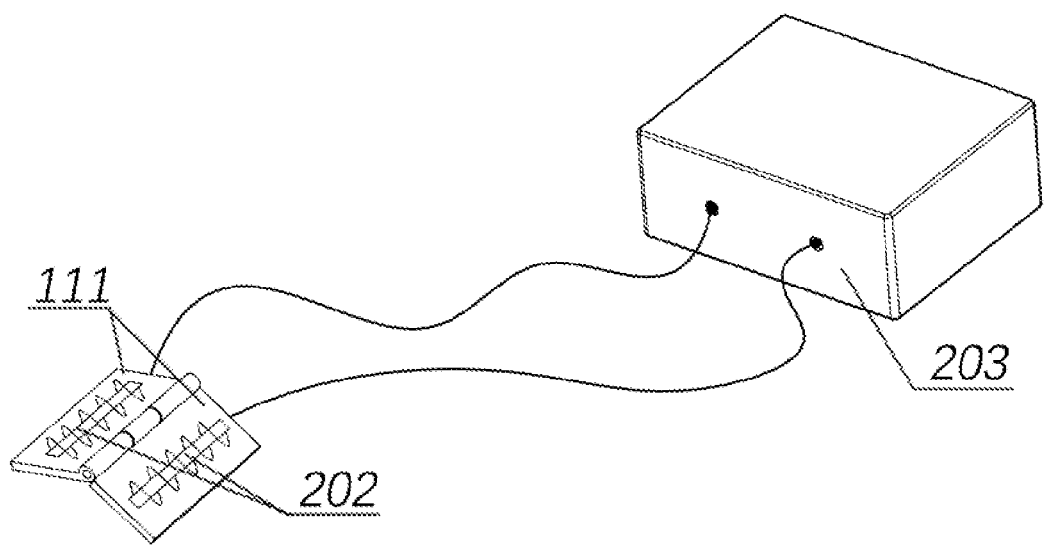
FIG. 8 is a schematic diagram of a plane calibration tool according to a fourth example of Embodiment 1 of the present application.
Figure 9:
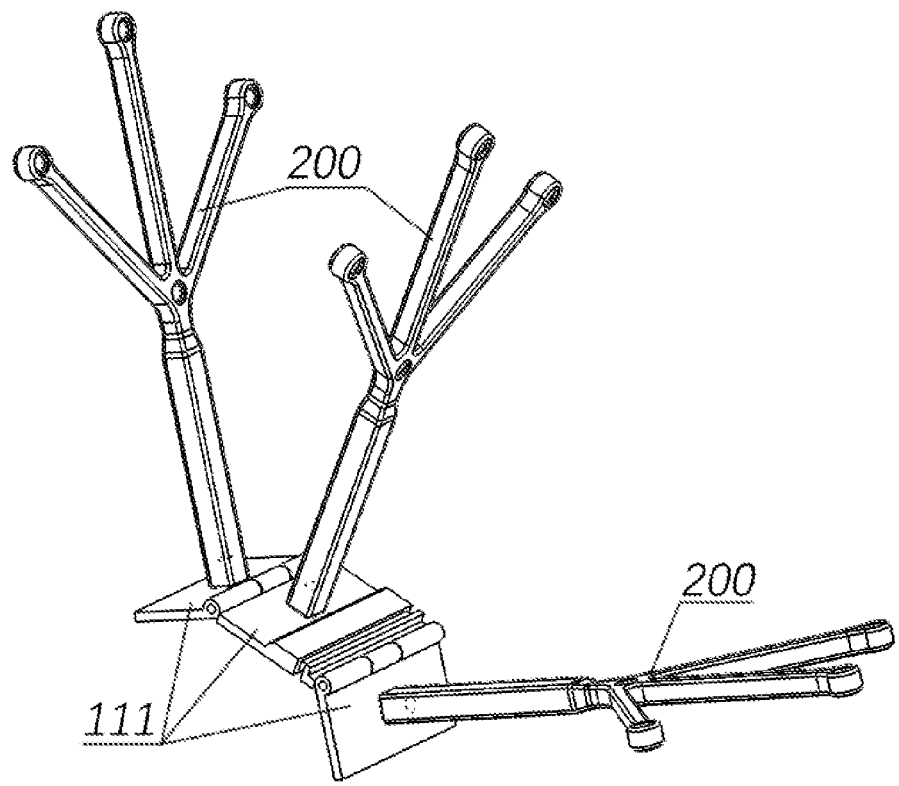
FIG. 9 is a schematic diagram of a plane calibration tool according to a fifth example of Embodiment 1 of the present application.
Figure 10:
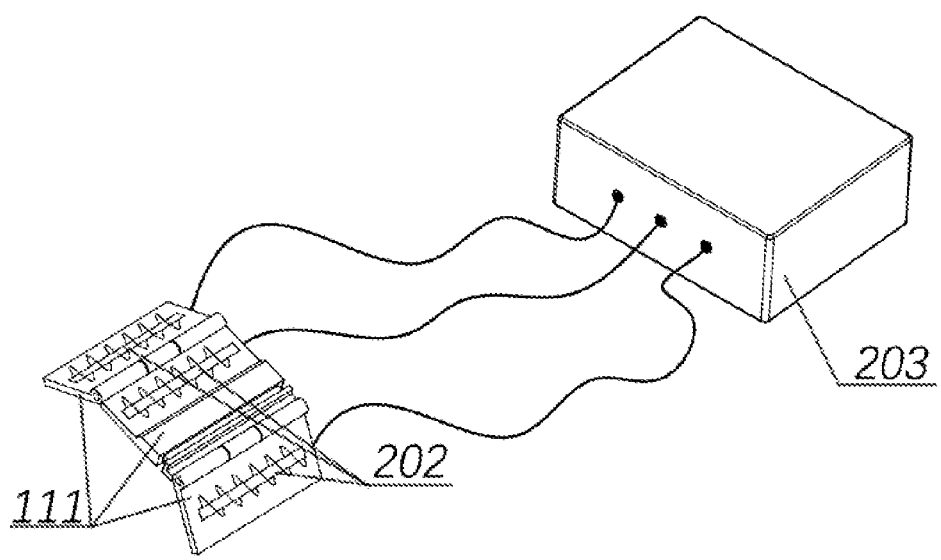
FIG. 10 is a schematic diagram of a plane calibration tool according to a sixth example of Embodiment 1 of the present application.
Figure 11:
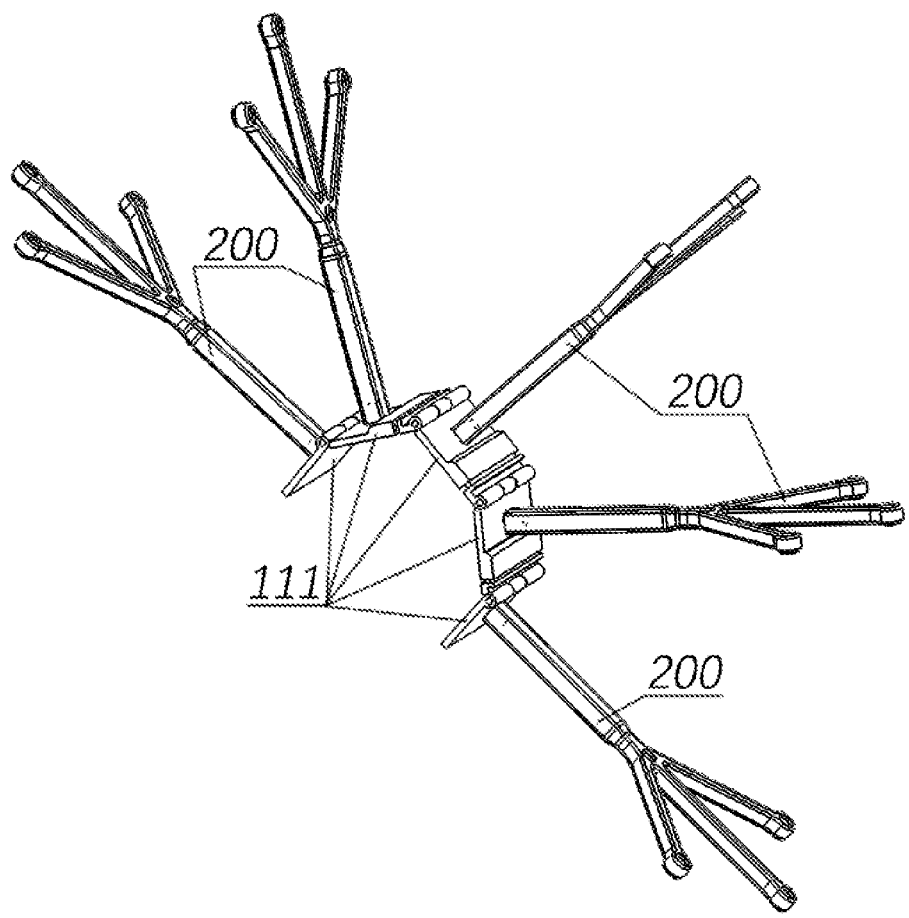
FIG. 11 is a schematic diagram of a plane calibration tool according to a seventh example of Embodiment 1 of the present application.
Figure 12:
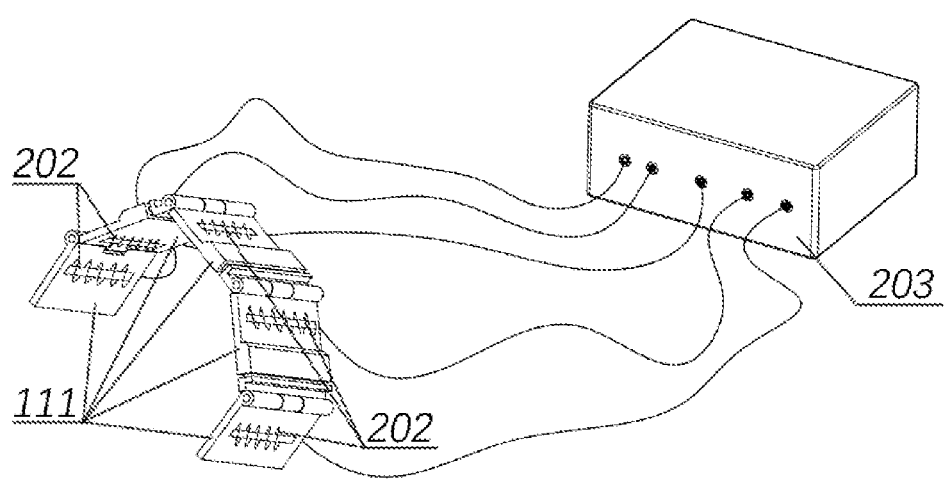
FIG. 12 is a schematic diagram of a plane calibration tool according to an eighth example of Embodiment 1 of the present application.

Referring to FIGS. 1 to 12, FIG. 1 is a schematic diagram of knee arthroplasty by using orthopedic surgery system provided by Embodiment 1 of the present application; FIG. 2 is a flowchart of an osteotomy calibration method provided by Embodiment 1 of the present application; FIG. 3 is a schematic diagram of a plane calibration tool provided by a first example of Embodiment 1 of the present application; FIG. 4 is a schematic diagram of usage of a plane calibration tool provided by a first example of Embodiment 1 of the present application; FIG. 5 is a schematic diagram of a plane calibration tool provided by a second example of Embodiment 1 of the present application; FIG. 6 is a schematic diagram of a plane calibration tool provided by a third example of Embodiment 1 of the present application; FIG. 7 is a schematic diagram of usage of a plane calibration tool provided by a third example of Embodiment 1 of the present application; FIG. 8 is a schematic diagram of a plane calibration tool provided by a fourth example of Embodiment 1 of the present application; FIG. 9 is a schematic diagram of a plane calibration tool provided by a fifth example of Embodiment 1 of the present application; FIG. 10 is a schematic diagram of a plane calibration tool provided by a sixth example of Embodiment 1 of the present application; FIG. 11 is a schematic diagram of a plane calibration tool provided by a seventh example of Embodiment 1 of the present application; FIG. 12 is a schematic diagram of a plane calibration tool provided by a eighth example of Embodiment 1 of the present application.

Embodiment 1 of the present application provides an orthopaedic surgical system. FIG. 1 shows a schematic diagram of knee arthroplasty by using the orthopaedic surgical system. However, the orthopaedic surgical system of the present application has no particular limitation on the application environment and can also be applied to other orthopedic surgery. In the following description, an orthopaedic surgical system is described by using knee joint arthroplasty as an example, but it should not be used to limit the present application.

As shown in FIG. 1, the orthopedic surgery system includes a control device, a navigation device, a robotic arm 2, and an osteotomy navigation tool 4. The control device is a computer in some embodiments, but the present application is not limited thereto. The computer is equipped with a controller, a main display 8 and a keyboard 10, and more preferably also includes an auxiliary display 7. In this embodiment, the contents displayed on the auxiliary display 7 and the main display 8 are the same, for example, both are used to display an osteotomy position image. The navigation device is selected as an electromagnetic positioning navigation device, an optical positioning navigation device, or an electromagnetic positioning navigation device. Preferably, the navigation device is an optical positioning navigation device. Compared with other navigation methods, the optical positioning navigation has a high measurement accuracy, which can effectively improve the positioning accuracy of the osteotomy navigation tool. In the following description, the optical positioning and navigation device is taken as an example for description, but is not limited thereto.

The navigation device includes a navigation marker and a tracker 6. The navigation marker includes a base trackable element 15 and a tool trackable element 3. The base trackable element 15 is fixed, for example, the base trackable element 15 is fixed on the surgical trolley 1 to provide a base coordinate system (also referred to as a base trackable element coordinate system). The tool trackable element 3 is mounted on the osteotomy navigation tool 4 to track the position of the osteotomy navigation tool 4. The osteotomy navigation tool 4 is installed at the end of the robotic arm 2 so that the osteotomy navigation tool 4 is supported by the robotic arm 2 and the spatial position and pose of the osteotomy navigation tool 4 are adjusted.

In practice, the tracker 6 is used to capture the signal (such as an optical signal) reflected by the tool trackable element 3 and record the position of the tool trackable element 3 (that is, the position and pose of the tool trackable element under the base trackable element system). The computer program stored in the memory of the control device controls the movement of the robotic arm 2 according to the current position and the desired position of the tool trackable element. The robotic arm 2 drives the osteotomy navigation tool 4 and the tool trackable element 3 to move so that the tool trackable element 3 reaches the desired position. The desired position of the tool trackable element 3 corresponds to the desired position of the osteotomy navigation tool 4.

Therefore, for the application of the orthopaedic surgery system, the automatic positioning of the osteotomy navigation tool 4 can be realized, and the real-time pose of the osteotomy navigation tool 4 is tracked and fed back by the tool trackable element 3 during the operation, and the adjustment of the position and pose of the osteotomy navigation tool 4 is achieved by controlling the movement of the robotic arm. The osteotomy navigation tool 4 not only achieves a high positioning accuracy, but also is supported by the robotic arm 2, that is, no need to fix the navigation tool to the human body, which can avoid the secondary or further injury to the human body.

Generally, the orthopedic surgery system further includes a surgical trolley 1 and a navigation trolley 9. The control device and a part of the navigation device are installed on the navigation cart 9, for example, the controller is installed inside the navigation cart 9, and the keyboard 10 is placed outside the navigation trolley 9 for operation. Each of the main display 8, the auxiliary display 7 and the tracker 6 is mounted on a bracket, the bracket is vertically fixed on the navigation trolley 9, and the robotic arm 2 is mounted on the surgical trolley 1. The use of the surgical trolley 1 and the navigation trolley 9 makes the entire surgical operation more convenient.

When performing knee arthroplasty surgery, the use of the orthopedic surgery system of this embodiment generally includes the following operations:

firstly, moving the surgical trolley 1 and the navigation trolley 9 to appropriate positions next to the hospital bed;

secondly, installing navigation markers (the navigation markers also include the femoral trackable element 11 and the tibial trackable element 13), the osteotomy navigation tool 4, and other related components (such as sterile bags);

thirdly, the operator 18 imports the CT/MR scan model of the bone of the patient 17 into the computer for preoperative planning so as to obtain an osteotomy plan which includes, for example, the coordinates of the osteotomy plane, the model of the prosthesis, and the installation orientation of the prosthesis and other information; specifically, based on the patient's knee joint image data obtained from the CT/MR scan, a three-dimensional digital model of the knee joint is created, and then an osteotomy plan is created based on the three-dimensional digital model of the knee joint, so that the operator can perform preoperative evaluation according to the osteotomy plane. More specifically, the osteotomy plan is determined based on the three-dimensional digital model of the knee joint, and the obtained prosthesis size specifications and the installation position of the osteotomy plate. The osteotomy plan is finally output in the form of a surgical report, which records a series of reference data such as osteotomy plane coordinates, osteotomy amount, osteotomy angle, prosthesis specifications, installation position of prosthesis, surgical aids, etc, especially includes a series of theoretical explanations, such as the reason for selection of the osteotomy angle and etc, so as to provide a reference for surgical operators. Among them, the three-dimensional digital model of the knee joint can be displayed on the main display 8 and the operator can input surgical parameters by keyboard 10 to facilitate preoperative planning;

after the preoperative evaluation, the operator 18 then uses the trackable element pen to mark feature points on the patient's femur and tibia (that is, the operator marks multiple femoral anatomical feature points on the patient's femoral, and multiple tibial anatomical features on the tibia), and the navigation device (taking the base trackable element 15 as a reference) is used to record the positions of all feature points on the patient's tibia 14 and femur 12, and send the positions of all feature points to the controller, and then the controller obtains the actual orientation of the femur 12 and the tibia 14 by matching algorithm. The actual orientation of the femur 12 and the tibia 14 corresponds to the CT/MR image orientation of the femur 12 and the tibia 14;

subsequently, the actual orientation of the femur and tibia is linked to the corresponding trackable element mounted on the femur and tibia through the navigation device, so that the femoral trackable element 11 and the tibia trackable element 13 can track the actual position of the bone in real time. During the surgery, as long as the relative position of the trackable element with respect to the bone is fixed, the bone movement will not affect the surgical effect;

further, the coordinate of the osteotomy plane planned before the operation is sent to the robotic arm 2 through the navigation device. After the robotic arm 2 locates the osteotomy plane through the tool trackable element 3 and moves to the predetermined position, the robotic arm 2 keeps in the holding state (that is, does not move)). After that, the operator can perform osteotomy and/or drilling operations with the osteotomy navigation tool 4 by using a surgical tool 5 such as a pendulum saw or an electric drill. After the osteotomy and drilling operations have been completed, the operator can install the prosthesis and perform other surgical operations.

Traditional surgery and navigation surgery systems without robotic arm for positioning require manual adjustment of the osteotomy navigation positioning tool, which has a poor accuracy and a low adjustment efficiency. With the use of a robotic arm positioning navigation tool, the operator does not need to fix the navigation tool on the bones by additional bone nail, so that the patient's trauma surface and the operation time are reduced.

In this embodiment, the navigation marker further includes a femur trackable element 11 and a tibial trackable element 13. The femoral trackable element 11 is used to locate the spatial position and pose of the femur 12, and the tibial trackable element 13 is used to locate the spatial position and pose of the tibia 14. As mentioned before, the tool trackable element 3 is mounted on the osteotomy navigation tool 4, but in other embodiments, the tool trackable element 3 may also be mounted on the end joint of the robotic arm 2.

Based on the above orthopedic surgery system, robot-assisted surgery can be achieved, which helps the operator to locate the osteotomy position so that to facilitate the osteotomy. After the operator performs the osteotomy by an orthopaedic surgical system or other methods (such as performing the osteotomy manually without robotic assistance), multiple osteotomy planes can be obtained, hereinafter referred to as the current osteotomy plane. As described in the Background, accuracy of the current osteotomy plane is limited due to reasons such as positioning accuracy of the robotic arm and saw blade swing. Therefore, as shown in FIG. 2, this embodiment provides an osteotomy verification method, including:

step S1: calculating a position information of a detection plane of a plane calibration tool placed on a current osteotomy plane, and defining the position information of the detection plane as a calculated position information of the current osteotomy plane;

step S2: determining a position error between the calculated position information and a predetermined position information based on a planned osteotomy plane, and if the position error exceeds a preset value, calculating and obtaining a relocation information, and transmitting the relocation information to a robotic arm so as to control and relocate the robotic arm.

To achieve the above osteotomy calibration method, this embodiment provides a plane calibration tool including one or more detection planes and at least one trackable element. The trackable element is disposed on at least one of the detection planes, and the trackable element is fixed in position with respect to the detection plane. The detection plane is configured to be placed on a current osteotomy plane to obtain the position information of the current osteotomy plane. The navigation device matches with the trackable element to determine a position information of the trackable element itself through a communicating connection between the trackable element and the navigation device, and the position information of the trackable element is provided to the control device to subsequently calculate the position information of the detection plane. Apparently, the relative positional relationship between the trackable element and the detection plane referred to here is fixed, and it is not limited that those two must be fixedly connected, rather the relative positional relationship therebetween after assembly is fixed. In some embodiments, the detection plane and the trackable element is detachably connected. When the plane calibration tool is deformed or the detection plane needs to be replaced, the detection plane can be directly replaced without replacing the entire plane calibration tool. Further, the orthopedic surgery system includes the plane calibration tool as described above. The navigation device 6 matches with the trackable element 200 of the plane calibration tool so as to obtain a position information of the trackable element 200 and feedback the position information to the control device; the control device is configured to obtain a calculated position information of a current osteotomy plane according to the position information of the trackable element 200 of the plane calibration tool, and to determine a position error between the calculated position information and a predetermined position information of a planned osteotomy plane, and if the position error exceeds a preset value, the control device drives and relocates the robotic arm 2. Specifically, the position error is superimposed on the predetermined position information to obtain relocation information, and the relocation information is transmitted to the robotic arm 2 so as to relocate the robotic arm.

Referring to FIG. 3, in a first example of this embodiment, the plane calibration tool includes a detection plane and a trackable element 200, and the trackable element 200 is arranged on the detection plane. Hereinafter, the detection plane on which the trackable element 200 is arranged is referred to as a first detection plane 111. Optionally, the trackable element 200 includes four reflective spheres 201, and the four reflective spheres 201 form a geometric array which is recognized by the optical navigation system NDI (that is, the aforementioned navigation device). The relative position of the first detection plane 111 with respect to the trackable element 200 is fixed, and the relative positional relationship is stored in a storage device in advance. Specifically, the optical navigation system is configured to receive/track the information fed back by the reflective sphere 201 on the trackable element 200, thus the position information of the trackable element 200 is obtained, and then the position information is sent to the control device. The control device according to the prestored positional relationship of the trackable element with respect to the detection plane, calculating a position information of a detection plane, and defining the position information of the detection plane as a calculated position information of the current osteotomy plane; determining a position error between the calculated position information and a predetermined position information (stored in a storage device in advance) based on a planned osteotomy plane, and if the position error exceeds a preset value, calculating and transmitting a relocation information to a robotic arm 2 so as to control and relocate the robotic arm 2. Preferably, three mark points are provided on the first detection plane 111. Before obtaining the calculated position information of the current osteotomy plane by using a plane calibration tool, the osteotomy calibration method includes: calibrating a relative position of the first detection plane 111 with respect to the trackable element 200. Of course, in some embodiments, after obtaining the calculated position information of the current osteotomy plane by using a plane calibration tool, calibrating a relative position of the first detection plane 111 with respect to the trackable element 200. In some embodiments, calibrating a plurality of marked points (e.g. three marked points 111a) on the first detection plane 111 by using a trackable tool with tips, so that the coordinates of the three marked points 111a in the reflective spherical coordinate system are obtained, calculating a real position and a real normal vector of the first detection plane 111, comparing the real position and the real normal vector with original data (factory data) so as to detect whether the plane calibration tool is deformed. If the plane calibration tool has deformed, it is calibrated or replaced by another undeformed plane calibration tool.

Further, the calculated position information includes a calculating normal vector and a calculated position, and the step of calculating the position information of the first detection plane 111 includes: determining a calculating normal vector $\vec{n}_V$ and a calculated position $P_V(x_V, y_V, z_V)$ of the detection plane in a lower limb DICOM data coordinate system based on a normal vector $\vec{n}_P$ and a position $P_P(x_P, y_P, z_P)$ of the first detection plane 111 in a trackable element coordinate system (that is the reflective spherical coordinate system) of the plane calibration tool, and a transformation matrix $M_{P \rightarrow V}$ between the trackable element coordinate system and the lower limb DICOM (Digital Imaging and Communications in Medicine) data coordinate system. As shown in FIG. 4, optionally, when coordinate transformation is performed between the trackable element coordinate system and the lower limb DICOM data coordinate system, femoral (or tibia) trackable element coordinate system is indirectly used due to the trackable element on the femur (or tibia) and the trackable element 200 of plane calibration tool in the optical navigation system NDI has their own position and pose information. Specifically, firstly through the transformation matrix $M_{P \rightarrow V}$ between the trackable element coordinate system and the femur (or tibia) trackable element coordinate system, the normal vector $\vec{n}_P$ and the position $P_P(x_P, y_P, z_P)$ of the first detection plane 111 in the trackable element coordinate system are transferred into a normal vector $\vec{n}_B$ and a position $P_B(x_B, y_B, z_B)$ in the femur (or tibia) trackable element coordinate system, then the normal vector $\vec{n}_B$ and the position $P_B(x_B, y_B, z_B)$ of the first detection plane 111 in femur (or tibia) trackable element coordinate system are transferred into the calculating normal vector $\vec{n}_V$ and the calculated position $P_V(x_V, y_V, z_V)$ in the lower limb DICOM data coordinate system through a transformation matrix $M_{B \to V}$ between femur (or tibia) reflective spherical coordinate system and the lower limb DICOM data coordinate $P_V(x_V, y_V, z_V)$.

Further, the position error includes: a normal vector rotation matrix of the calculating normal vector and a predetermined normal vector based on the predetermined normal vector and the predetermined position of the planned osteotomy plane; and a position deviation between the calculated position and the predetermined position of the planned osteotomy plane. Specifically, the calculating normal vector $\vec{n}_V$ and the calculated position $P_V(x_V, y_V, z_V)$ of the first detection plane 111 in a lower limb DICOM data coordinate system are respectively compared with the predetermined normal vector $\vec{n}_O$ and the predetermined position $P_O(x_O, y_O, z_O)$ of the planned osteotomy plane. Through two normal vectors, an euler angle between the first detection plane 111 and the planned osteotomy plan is obtained, thereby obtaining the rotation matrix $R_{3\times3}$. Rotating the first detection plane 111 to be parallel to the planned osteotomy plane through the rotation matrix $R_{3\times3}$ and a distance $\vec{d}$ between the two planes is calculated. The normal vector rotation matrix $R_{3\times3}$ and the position deviation $\vec{d}$ is the position error between the first detection plane 111 and planned osteotomy plane. Since the first detection plane 111 is placed on the current osteotomy plane, the normal vector rotation matrix $R_{3\times3}$ and the position deviation $\vec{d}$ are the position error between the current osteotomy plane and the planned osteotomy plane.

Furthermore, after determining the position deviation between the calculated position and the predetermined position of the planned osteotomy plane, if at least one of the normal vector rotation matrix $R_{3\times3}$ (the amount of rotation of each axis after the normal vector rotation matrix $R_{3\times3}$ transformed into the euler angle) and the position deviation $\vec{d}$ exceeds a preset value, then the normal vector rotation matrix $R_{3\times3}$ and the position deviation $\vec{d}$ are superimposed on the predetermined position information to obtain relocation information, and transmitting the relocation information to a robotic arm so as to control and relocate the robotic arm. Those skilled in the art can set an appropriate preset value to the normal vector rotation matrix $R_{3\times3}$ and the position deviation $\vec{d}$ according to the actual situation, when at least one of the normal vector rotation matrix $R_{3\times3}$ and the position deviation $\vec{d}$ exceeds the preset value, it can be considered that the accuracy of the current osteotomy plane formed by the first osteotomy does not meet the requirements, and a second osteotomy is required. Thus the normal vector rotation matrix $R_{3\times3}$ and the position deviation $\vec{d}$ are transmitted to robotic arm 2 so as to relocate the robotic arm 2, and a further osteotomy is performed. Therefore, a more accurate osteotomy result is obtained. Contrarily, if each of the normal vector rotation matrix $R_{3\times3}$ and the position deviation $\vec{d}$ is in accordance with the preset values, that is, the accuracy of the current osteotomy plane meets the requirements, and the surgical procedure can be continued.

It should be understood that in the above description, four reflective spheres are schematically used as the trackable element 200. The arrangement of the reflective spheres is not limited to a rectangular distribution as shown in FIG. 3, it can also be distributed like a tree as shown in FIG. 4, and the number of reflective spheres is not limited to four as well. It should be noted that the trackable element 200 is not limited to the form of an optical trackable element sphere. As shown in FIG. 5, in the second example of this embodiment, the magnetic coil 202 is used as the trackable element 200. Specifically, a 5DOF coil can be used as the trackable element 200, and the end of the cable of the coil is connected to the SIU module 203. In this configuration, the navigation device can use the NDI magnetic navigation AURORA. In this way, the position information of the trackable element 200 is also obtained by sensing the position and orientation of the coil.

It should be understood that the above osteotomy calibration is performed after each osteotomy step is completed, or it is performed at one time after multiple osteotomy steps are completed. The timing of osteotomy calibration is determined according to operating habits, that is to say, when to perform the osteotomy calibration is determined according to operating habits. In some embodiments, the plane calibration tool includes two or more first detection planes 111, and each of the first detection planes 111 is provided with a trackable element 200, wherein the two or more first detection planes 111 are rotatably connected in sequence, and if the first detection planes 111 are more than two, a length of at least a middle one of the first detection planes 111 is adjustable. Please refer to FIG. 6 and FIG. 7, in the third example of this embodiment, the plane calibration tool includes two first detection planes 111, each of first detection planes 111 is provided with a trackable element 200 (preferably reflective sphere trackable elements), the two first detection planes 111 are used to check the two current osteotomy planes. In practice, performing an osteotomy on the end of the femur or tibia usually results in an osteotomy plane with multiple angles for subsequent prosthesis installation. In this example, the two first detection planes 111 can be respectively placed on two current osteotomy planes. Since each of the two first detection planes 111 is provided with a trackable element 200, the control device obtains position information of the two first detection plane 111 based on the position information of the trackable element 200 obtained by the navigation device 6, further obtaining the calculated position information of the two current osteotomy planes corresponding to the two first detection planes 111. After obtaining the calculated position information of the two current osteotomy planes, with reference to the foregoing method, the calculated position information of the two current osteotomy planes is compared with the predetermined position information of the planned osteotomy plane and further transmitted for subsequent use for the second osteotomy. Please refer to the previous method for details, which will not be repeated here. Since the plane calibration tool includes a plurality of first detection planes 111, preferably, in this exemplary example, the calibration step may be performed at one time after completing the multiple osteotomy steps. Since the first detection planes 111 are rotatably connected in sequence, the calibration step is performed after each osteotomy step is completed. Please refer to FIG. 8, in a fourth example of this embodiment, the magnetic coil 202 is used as the trackable element 200, each of the first detection planes 111 is provided with a magnetic coil 202 used as the trackable element 200. Please refer to the second example of this embodiment for details.

Referring to FIG. 9, in a fifth example of this embodiment, the plane calibration tool includes three first detection planes 111, and each of the first detection planes 111 is provided with a trackable element 200, and the trackable element 200 is preferably a reflective sphere trackable element. The three first detection planes 111 are rotatably connected in sequence, and the length of a middle one of the first detection planes 111 is adjustable, so as to match with the three current osteotomy planes for calibration. In actual practice, each of the three first detection planes 111 abuts on a current osteotomy plane. Please refer to FIG. 10, in a sixth example of this embodiment, the magnetic coil 202 is used as the trackable element 200, each of the first detection plane 111 is provided with a magnetic coil 202 as trackable element 200. Similarly, referring to FIG. 11 and FIG. 12, which are schematic diagrams of a seventh example and an eighth example of this embodiment. In a seventh example of this embodiment, a plane calibration tool includes five first detection plane 111, each of the first detection planes 111 is connected to a trackable element 200, which is preferably a reflective sphere trackable element, five first detection planes 111 are rotatably connected in sequence, and the length of three first detection planes 111 located in the middle is adjustable for calibrating five current osteotomy planes. Specifically, the each of the three first detection planes 111 includes a telescopic device. In the eighth example, the magnetic coil 202 is used as the trackable element 200, each of the first detection plane 111 is provided with a magnetic coil 202 as trackable element 200. The principles of the fifth to eighth examples are the same as those of the third and fourth examples. Since each of the first detection planes 111 is provided with a trackable element 200, the navigation device obtains position information of each of the first detection planes 111, and then calculating the calculated position information of the current osteotomy plane corresponding to each of the first detection planes 111. Please refer to the above description for details.

According to the above method, by calculating and identifying the position error between the current osteotomy plane formed by the first osteotomy and the planned predetermined osteotomy plane, the robotic arm 2 is relocated, and then the osteotomy plane is corrected twice, which can improve the final oteotomy plane accuracy. By relocating the robotic arm 2 and performing the secondary correction of the osteotomy plane, additional bone nails which is to fix the navigation tool to the bone can be avoided. Therefore, the patient's trauma surface and surgical time can be reduced. Of course, the calibration can be performed immediately after an osteotomy is completed, or it can be performed at one time after all the osteotomy steps are completed. Based on this, Embodiment I also provides a readable storage medium on which a program is stored, and when the program is executed, the above-mentioned osteotomy calibration method is implemented. Alternatively, the above program is integrated into a hardware device, such as integrated into the control device of an orthopaedic surgical system.

Embodiment 2

Figure 13:
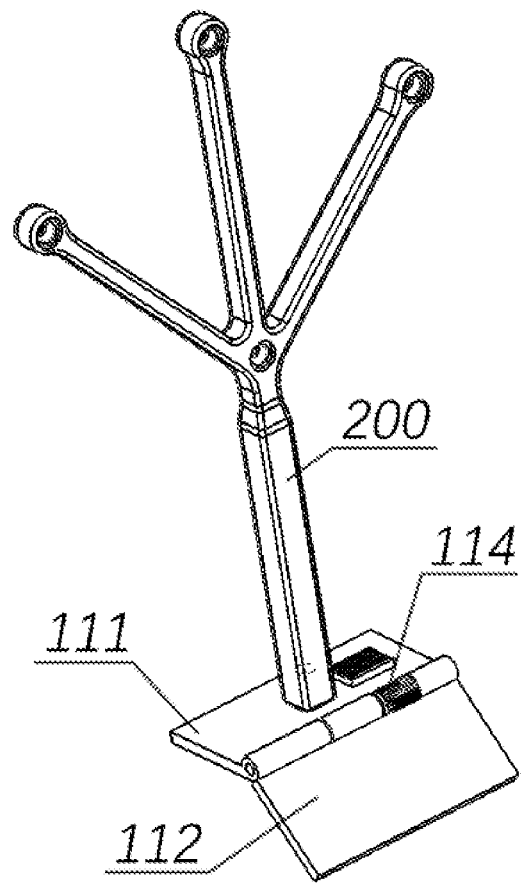
FIG. 13 is a schematic diagram of a plane calibration tool according to a first example of Embodiment 2 of the present application.
Figure 14:
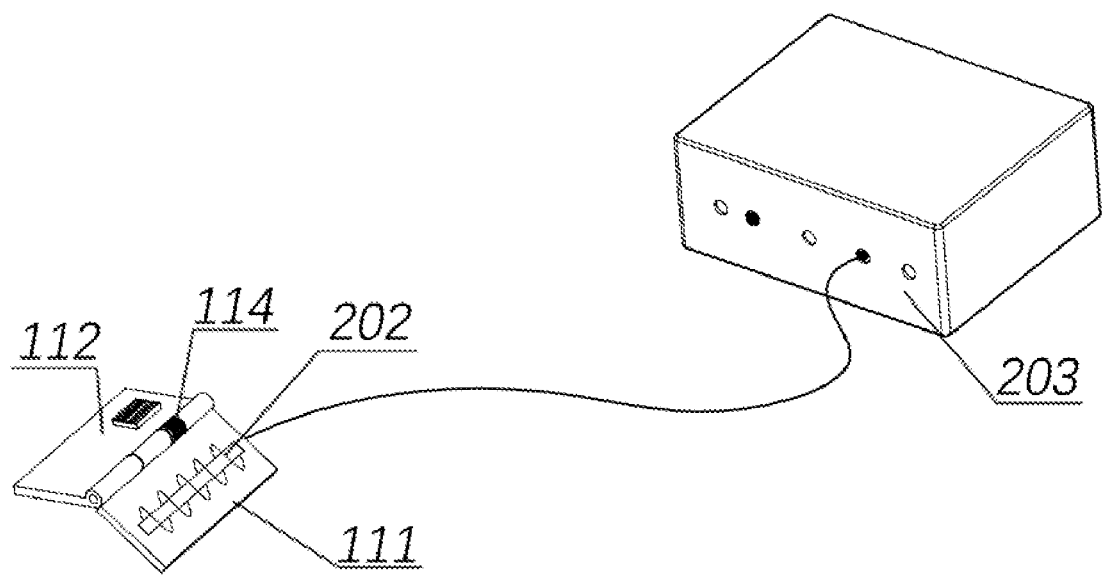
FIG. 14 is a schematic diagram of a plane calibration tool according to a second example of Embodiment 2 of the present application.
Figure 15:
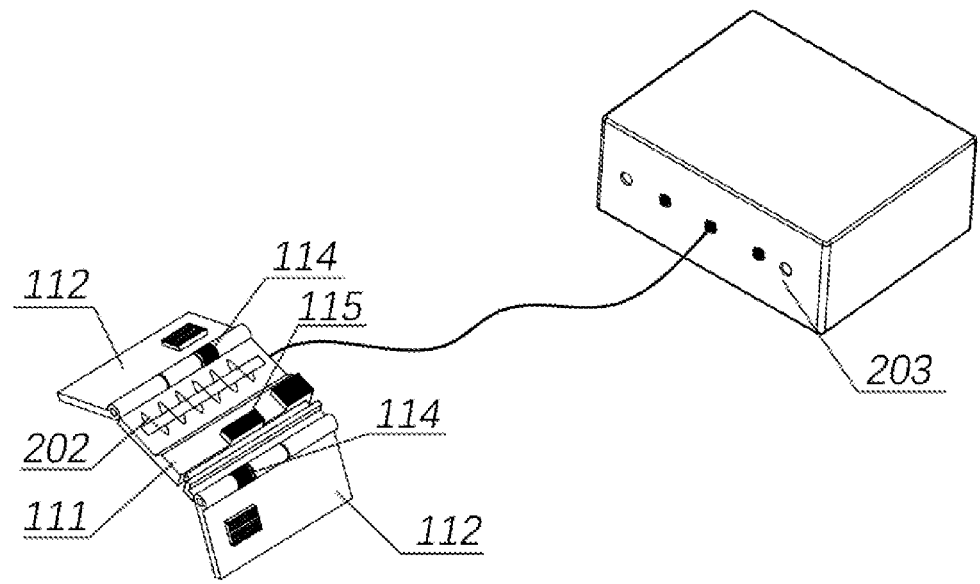
FIG. 15 is a schematic diagram of a plane calibration tool according to a third example of Embodiment 2 of the present application.
Figure 16:
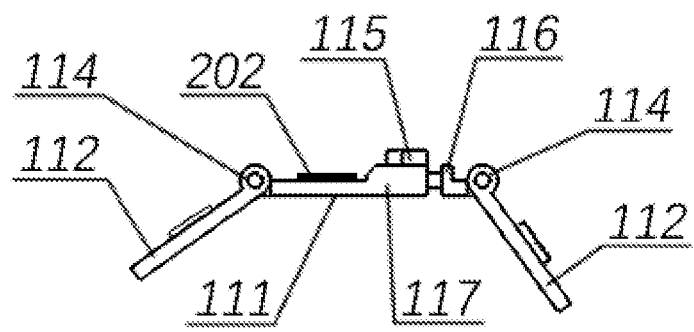
FIG. 16 is a side view of the plane calibration tool as shown in FIG. 15.
Figure 17:
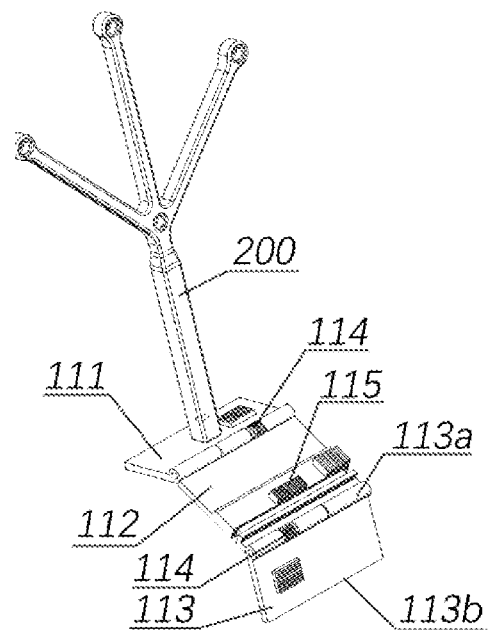
FIG. 17 is a schematic diagram of a plane calibration tool according to a fourth example of Embodiment 2 of the present application.
Figure 18:
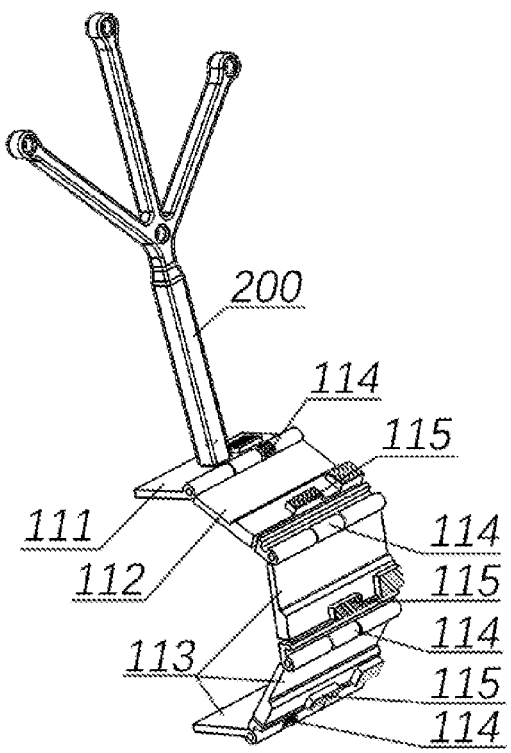
FIG. 18 is a schematic diagram of a plane calibration tool according to a fifth example of Embodiment 2 of the present application.
Figure 19:
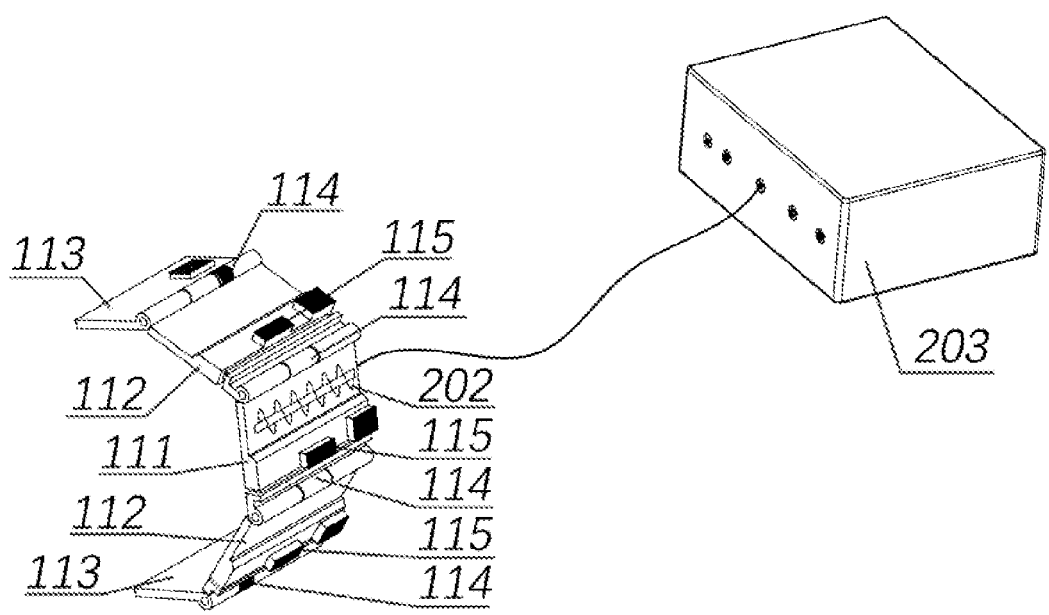
FIG. 19 is a schematic diagram of a plane calibration tool according to a sixth example of Embodiment 2 of the present application.

Referring to FIG. 13 to FIG. 19, where FIG. 13 is a schematic diagram of a plane calibration tool provided by a first example of Embodiment 2 of the present application, FIG. 14 is a schematic diagram of a plane calibration tool provided by a second example of Embodiment 2 of the present application, FIG. 15 is a schematic diagram of a plane calibration tool provided by a third example of Embodiment 2 of the present application, FIG. 16 is a side view of the plane calibration tool of FIG. 15, FIG. 17 a schematic diagram of a plane calibration tool provided by a fourth example of Embodiment 2 of the present application, FIG. 18 is a schematic diagram of a plane calibration tool provided by a fifth example of Embodiment 2 of the present application, FIG. 19 is a schematic diagram of a plane calibration tool provided by a sixth example of Embodiment 2 of the present application.

The osteotomy calibration method, calibration tools, a readable storage medium, and an orthopedic surgery system provided by Embodiment 2 are substantially similar to those provided by Embodiment 1. Basically the same parts will not be described, only the differences will be described below.

In Embodiment 2, the plan calibration tool includes two or more detection planes rotatably connected in sequence, wherein at least one of the detection planes is provided with the trackable element 200 and is defined as a first detection plane 111, and one or more detection planes adjacent to the first detection plane 111 are defined as second detection planes 112, wherein a distance between the trackable element 200 of the first detection plane 111 and an adjacent one of the second detection planes 112 is fixed, and wherein an angle sensor 114 is arranged therebetween and configured to sense an angle between the first detection plane 111 and the adjacent one of the second detection planes 112. Further, when the plane calibration tool includes three or more detection planes rotatably connected in sequence, a length of at least a middle one of the detection planes is adjustable.

In Embodiment 2, the plane calibration tool not only includes the first detection plane 111 provided with the target 200, but also the second detection plane 112 adjacent to the first detection plane 111, wherein the second detection plane is not provided with the trackable element 200 directly. Based on the above configuration, in the osteotomy calibration method provided in this embodiment, calculating the position information of the first detection plane 111 and the second detection plane 112 includes: calculating a position information of the detection plane (that is, the first detection plane 111) provided with trackable element 200; acquiring an angle between the first detection plane 111 and the second detection plane 112 adjacent to the first detection plane; calculating a position information of the second detection plane 112 according to the angle.

Referring to FIG. 13, in the first example of Embodiment 2, the plane calibration tool includes a first detection plane 111 and a second detection plane 112. The first detection plane 111 and the second detection plane 112 rotatably connected (that is, similar to a hinged connection) are respectively placed on two current osteotomy planes. The first detection plane 111 is provided with a trackable element 200. The trackable element 200 is preferably a reflective sphere trackable element. An angle sensor 114 is provided between the detection plane 111 and the second detection plane 112. The angle sensor 114 is disposed at the connection (such as on a hinge) between the first detection plane 111 and the second detection plane 112. The angle sensor 114 can sense the angle between the second detection plane 112 and the first detection plane 111, and transmits the data of the angle to the control device through a bluetooth transmission device or the like.

Since the first detection plane 111 is connected to a trackable element 200, the normal vector $\vec{n}_{P1}$ and position $P_{P1}$ ($x_{P1}$, $y_{P1}$, $z_{P1}$) of the first detection plane 111 in the trackable element coordinate system of the plane calibration tool (that is, the reflective spherical coordinate system) are obtained. The data of the normal vector $\vec{n}_R$ of rotation axis installed with the angle sensor 114 in the trackable element coordinate system is calibrated at the factory, that is, the normal vector $\vec{n}_R$ of the rotation axis installed with the angle sensor 114 is known. Based on the angle that is provided by sensor 114 and is between the second detection plane 112 and the first detection plane 111, a rotation angle θ of the second detection plane 112 with respect to the first detection plane 111 is obtained. The rotation angle is an angle rotating about the normal vector $\vec{n}_R$ of the rotation axis. According to this, an equivalent rotation matrix $T_{4\times 4}$ can be calculated, the normal vector of the second detection plane 112 is to be calculated based on $\vec{n}_{P2} = -\vec{n}_{P1} \cdot T_{4\times 4}$. In some embodiments, the rotary connection device adjacent to the first detection plane 111 is configured to be a readable device. During calibration, the visual reading is input into the corresponding position of the control device through the input device, and the control device calculates the equivalent rotation matrix $T_{4\times 4}$ according to the angle.

Further, according to the position $P_{P1}$ of the first detection plane 111, position of the rotation axis $P_{P0}$, the position $P_{P2}$ of the second detection plane 112 is determined by sides of the triangle $|P_{P2}P_{P0}|$, $|P_{P1}P_{P0}|$ and the angle θ between the first detection plane 111 and the second detection plane 112. Thus, the position information of the second detection plane 112 is calculated based on the angle sensed by the angle sensor 114 and the position information of the first detection plane 111.

The position information of the first detection plane 111 and the second detection plane 112 substantially represents the calculated position information of the two current osteotomy planes. When obtaining the calculated position information of the two current osteotomy planes, please refer to Embodiment 1, comparing and calculating the calculated position information of the two current osteotomy planes with the predetermined position information of the planned osteotomy plane for subsequent secondary osteotomy. For details, please refer to the foregoing method, which are omitted herein.

Referring to FIG. 14, in a second example of Embodiment 2, the magnetic coil 202 is used as the trackable element 200, and the trackable element 200 is disposed on the first detection plane 111. In the second example of Embodiment 2, the magnetic coil 202 replaces the reflective sphere trackable element in the first example. Please refer to the Embodiment 1 for specific structure and principle of the trackable element 200. For the principle of calculating the position information of the second detection plane 112 by using the first detection plane 111 and the angle sensor 114, please refer to the first example of Embodiment 2.

Referring to FIG. 15 and FIG. 16, in a third example of Embodiment 2, the plane calibration tool includes a first detection plane 111 and two second detection planes 112. The first detection plane 111 is rotatably connected to two adjacent second detection planes 112, which are arranged in the order of the second detection plane 112, the first detection plane 111, and the second detection plane 112. That is, the first detection plane 111 is located in the middle, and two second detection planes 112 are located on both sides of the first detection plane 111, and the length of the first detection plane 111 located in the middle is adjustable so as to adapt to the calibration of the three current osteotomy planes. The angle sensor 114 is provided at the connection between the first detection plane 111 and the second detection planes 112, and the three detection planes are respectively used to be placed on three current osteotomy planes. The plane 111 is provided with a trackable element 200. The trackable element 200 is a magnetic coil 202. The angle sensor 114 is provided between the first detection plane 111 and the two second detection planes 112. The first detection plane 111 is also provided with a displacement sensor 115. The first detection plane 111 includes a fixed section 117 and a telescopic section 116 (as shown in FIG. 16), and the telescopic section 116 is telescopically connected to the fixed section. The fixed section 117 is provided with a feedback part of the displacement sensor 115, which is used to feedback the relative distance between the telescopic section 116 and o the fixed section 117. According to the telescopic between the fixed section and the telescopic section 116, the length of the entire first detection plane 111 is adjustable. Further, the trackable element 200 (magnetic coil 202 in the example) is provided on the fixed section 117 of the first detection plane 111. The length change of the first detection plane 111 is generated between the fixed section 117 and the telescopic section 116, and the distance between the second detection plane 112 connected to the fixed section 117 and the trackable element 200 is fixed, so that the second detection plane 112 can only rotate with respect to the fixed section 117. Therefore, according to the description of the first example of Embodiment 2, the position information of the second detection plane connected to the fixed section 117 can be calculated based on the position information of the first detection plane 111 and the angle between the second detection plane 112 connected to the fixed section 117 and the first detection plane 111. The distance of the second detection plane 112 connected to the telescopic section 116 with respect to the trackable element 200 is adjustable. The position information of the second detection plane 112 connected to the telescopic section 116 cannot be obtained directly from the position information of the first detection plane 111. Therefore, the displacement sensor 115 is also required to capture the displacement information $D_{12}$ representing the displacement of the second detection plane 112 connected to the telescopic section 116 with respect to the trackable element 200. Specifically, according to the position $P_{P1}$ of the first detection plane 111, the position of the rotation axis $P_{P0}$ of the second detection plane 112 connected to the telescopic section 116 and the first detection plane 111 as well as the angle $θ_{12}$ between the second detection plane 112 connected to the telescopic section 116 and the first detection plane 111, the position $P_{P2}$ of the second detection plane 112 connected to the telescopic section 116 is calculated according to sides of the triangle $|P_{P2}P_{P0}|$, $|P_{P1}P_{P0}+D_{12}|$ and angle $θ_{12}$. Thus, the position information of all the detection planes is calculated. In some embodiments, the displacement information $D_{12}$ is acquired by displacement sensor 115, preferably, transmitted to the control device through a bluetooth transmission device. In other embodiments, the telescopic section 116 includes a telescopic device capable of visual reading, such as a vernier caliper, and the user inputs the read data to corresponding position of the computer user interface of the control device, and the control program in the computer will automatically calculate the position deviation. In some embodiments, the angle sensor between each detection plane is a readable device. The user enters the displayable angle information into the computer user interface of the control device, and the control program in the computer will automatically calculate the euler angle.

In some other examples, the plane calibration tool includes two first detection planes 111 and a second detection plane 112, and the second detection plane 112 are rotatably connected to two adjacent first detection planes 112, which are arranged in the order of the first detection plane 111, the second detection plane 112, and the first detection plane 111. That is, the second detection plane 112 is located in the middle, and the two first detection planes 111 are located on two sides of the second detection plane 112. The length of the second detection plane 112 located in the middle can be adjusted so as to adapt to the calibration of the three current osteotomy planes. Between two connections of the second detection plane 112 and first detection planes 111, only one angle sensor 114 is provided on one of the connection, then the position information of the second detection plane 112 is calculated according to position information of the first detection plane 111. Therefore, in this case, it is not necessary to provide a displacement sensor. It is to be understood that when a larger number of the first detection planes 111 or the second detection planes 112 are provided, since the second detection plane 112 is adjacent to at least one of the first detection planes 111, the second detection plane 112 located in the middle must be adjacent to two first detection planes 111, only selecting one of the first detection plane 111 adjacent thereto to set the angle sensor 114, the position information of the second detection plane 112 can be calculated. When the second detection planes 112 are located at the head and tail of all detection planes, a displacement sensor 115 is provided on the first detection plane 111 connected to the second detection plane 112 by the telescopic section 116. For specific principles, please refer to the above description.

Preferably, the plane calibration tool further includes at least one third detection plane 113 (as shown in FIG. 17 and FIG. 18). The third detection plane 113 has a first side 113a and a second side 113b opposite to the first side. The first side 113a orients to the first detection plane 111, and the first side 113a and the first detection plane 111 are spaced apart by at least one second detection plane 112. Of course, in some embodiments, there are other multiple third detection planes 113 spaced apart from each other. The angle sensor 114 is provided between the third detection plane 113 and a detection plane adjacent to the first side 113a of the third detection plane 113 (it is to be understand that the detection plane adjacent to the first side 113a of the plane 113 is the second detection plane 112 or another third detection plane 113). The displacement sensor 114 is provided on a detection plane adjacent to the first side 113a of the third detection plane 113 (it is to be understand that the detection plane adjacent to the first side 113a of the plane 113 is the second detection plane 112 or another third detection plane 113). The displacement sensor 115 is configured to sense a displacement of the third detection plane 113 with respect to another one of the detection planes located at the first side 113a and indirectly adjacent to the third detection plane 113 (it is to be understand that the detection plane indirectly adjacent to the first side 113a of the plane 113 is the first second detection plane 111 or the second detection plane 112 or another third detection plane 113).

Referring to FIG. 17, in a fourth example of Embodiment 2, the plane calibration tool includes a first detection plane 111, a second detection plane 112, and a third detection plane 113. The first detection plane 111, the second detection plane 112 and the third detection plane 113 are rotatably connected in sequence. The three detection planes are respectively placed on the three current osteotomy planes. The first detection plane 111 is provided with a trackable element 200. The trackable element 200, selectively, is a reflective sphere trackable element. An angle sensor 114 is provided between the first detection plane 111 and the second detection plane 112 adjacent thereto, and another angle sensor 114 is provided between the second detection plane 112 and the third detection plane 113 adjacent thereto. A displacement sensor 115 is provided on the second detection plane 112. The two angle sensors 114 can respectively obtain the angle between the first detection plane 111 and the second detection plane 112, and the angle between the third detection plane 113 and the second detection plane 112. The displacement sensor 115 is to sense a displacement of the third detection plane 113 with respect to another one of the detection planes (that is, the first detection plane 111) located at the first side 113a and indirectly adjacent to the third detection plane 113. Based on the first example of Embodiment 2, the position information of the first detection plane 111 and the second detection plane 112 can be calculated based on the trackable element 200 and the angle between the first detection plane 111 and the second detection plane 112. Further, according to the angle between the three detection planes 113 and the second detection plane 112 and the displacement of the third detection plane 113 with respect to the first detection plane 111, the position information of the third detection plane 113 is calculated. For the calculation principles, please refer to the third example of Embodiment 2. The position $P_{P3}$ of the third detection plane 113 is obtained based on the position $P_{P2}$ of the second detection plane 112, the position $P_{P2}$ of the second detection plane 112 is obtained based on the position $P_{P1}$ of the first detection plane 111, the position $P_{P1}$ of the first detection plane 111 is obtained based on the trackable element 200, thereby forming the calculation of the position of each of the detection planes. As long as the position information of the trackable element 200 is obtained, the position information of all of the detection planes can be calculated in sequence.

Referring to FIG. 18, in a fifth example of Embodiment 2, the plane calibration tool includes a first detection plane 111, a second detection plane 112, and three third detection planes 113. The first detection plane 111, the second detection plane 112 and the three third detection planes 113 are rotatably connected in sequence and the side of each of the three third detection planes 113 oriented to the first detection plane 111 is defined as the first side 113a and the sides away from the first the detection plane 111 is defined as the second side 113b. The five detection planes are used to be placed on five current osteotomy planes respectively. The first detection plane 111 is provided with a trackable element 200, such as a reflective sphere trackable element. An angle sensor 114 is provided between first detection planes 111 and the second detection planes 112 adjacent thereto, another angle sensor 114 is provided between the second detection plane 112 and a third detection plane 113 adjacent thereto, and another angle sensor 114 is provided between all the third detection planes 113. Except for the first detection plane 111 and a third detection plane 113 located at the head and the tail respectively, all the other detection planes are provided with displacement sensors 115. For ease of description, the third detection plane 113 adjacent to the second detection plane 112 is defined as a first detection plane of the third detection plane 113, and the third detection plane 113 adjacent to the first detection plane of the third detection plane 113 is defined as a second detection plane of the third detection plane 113, and along the direction away from the first detection plane 111, the third detection plane 113 adjacent to the second detection plane of the third detection plane 113 is defined as a third detection plane of the third detection plane 113. Based on the fourth embodiment of Embodiment 2, the position information of the first detection plane 111, the second detection plane 112, and the first detection plane of the third detection plane 113 are calculated, and then based on the angle between the first detection plane of the third detection plane 113 and the second detection plane of the third detection plane 113, and the displacement of the second detection plane of the third detection plane 113 with respect to the second detection plane 112 (measured by the displacement sensor 115 on the first detection plane of the third detection plane 113), the position information of the second detection plane of the third detection plane 113 is calculated. It can be understood that the position information of the third detection plane of the third detection plane 113 can also be calculated based on the same method.

Referring to FIG. 19, in a sixth example of Embodiment 2, the plane calibration tool includes a first detection plane 111, two second detection planes 112, and two third detection planes 113. The detection planes are rotatably connected. The arrangement of the detection planes is in the order of: the third detection plane 113, the second detection plane 112, the first detection plane 111, the second detection plane 112, and the third detection plane 113. The side of the third detection plane 113 orienting to the first detection plane 111 is defined as the first side 113a, and being away from the first detection plane 111 is defined as the second side 113b. The five detection planes are respectively placed on the five current osteotomy planes. The first detection plane 111 is provided with a trackable element 200. The trackable element 200 is preferably a magnetic coil 202. The angle sensor 114 is provided between the first detection plane 111 and each of the adjacent detection planes 112. Another angle sensor 114 is provided between the second detection plane 112 and adjacent third detection plane 113. The displacement sensors 115 are respectively provided on the first detection planes located in the middle and the two detection planes 112. Optionally, the first detection plane 111 includes a fixed section and a telescopic section, and the trackable element 200 is disposed on the fixed section of the first detection plane 111. Based on the fourth example of Embodiment 2, the position information of the second detection plane 112 and the third detection plane 113 located at the side of the fixed segment can be calculated, and based on the third example of Embodiment 2, the position information of the second detection plane 112 located at the side of the telescopic section is calculated. Further, based on the fourth example of Embodiment 2, the position information of the second detection plane 112 connected to the telescopic section is known, then, the position information of the third detection plane 113 located at the side of the telescopic section is calculated. Thus, the position information of each of the detection planes is calculated.

Optionally, the plane calibration tool further includes a bluetooth transmitter for transmitting data sensed by the angle sensor and/or the displacement sensor to the control device so that the calculation is performed by the control device. Of course, those skilled in the art may also transmit data sensed by the angle sensor and/or the displacement sensor through other transmission methods.

It should be noted that, in this embodiment, the number of detection planes and the arrangement of the detection planes are not limited. The above-mentioned multiple examples are merely illustrations and not limitation. Those skilled in the art may use the method disclosed in this embodiment to arrange the angle sensors and/or displacement sensors at appropriate positions so as to obtain position information of all detection planes. In particular, the configuration of the trackable element, angle sensor, or displacement sensor may have a certain degree of redundancy than the minimum required number. In this way, the redundant trackable element, angle sensor, or displacement sensor can be used to calibrate the position information of the calculated detection plane. Therefore, the calculation accuracy of the detection plane is improved. The present application is not limited thereto.

It should be noted that each exemplary embodiment in the specification is described in a progressive manner. Each focuses on the differences from the others. For the same and similar parts therebetween, please refer to each other. In addition, different parts of the exemplary embodiments can also be used in combination, which is not limited in the present application.

In summary, in an osteotomy calibration method, calibration tools, a readable storage medium, and an orthopedic surgery system provided by the present application, firstly using the plane calibration tool to obtain the calculated position information of the current osteotomy plane, and then determining a position error between the calculated position information and a predetermined position information of a planned osteotomy plane, and if the position error exceeds a preset value, calculating and transmitting a relocation information to a robotic arm so as to control and relocate the robotic arm. In this way, by identifying the position error between the current osteotomy plane formed by the first osteotomy and the planned predetermined osteotomy plane, relocating the robotic arm, and performing a secondary correction of the osteotomy plane, which can improve the final accuracy of the osteotomy plane. In addition, by relocating the robotic arm and secondary correction of the osteotomy plane, additional bone nails which is to fix the navigation tool to the bone can be avoided. Therefore, the patient's trauma surface and surgical time can be reduced. The above description is only a description of the embodiments of the present application, and does not limit the scope of the present application. Any changes and modifications made by those skilled in the art in accordance with the above disclosure are within the scope of the claims.

What is claimed is:

1. A plane calibration tool, comprising at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking, wherein the plan calibration tool includes two or more detection planes, and each of the detection planes is provided with a trackable element, wherein the two or more detection planes are rotatably connected in sequence, and if the detection planes are more than two, a length of at least a middle one of the detection planes is adjustable.

2. A plane calibration tool, comprising at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking, wherein the plan calibration tool includes two or more detection planes rotatably connected in sequence, wherein at least one of the detection planes is provided with the trackable element and is defined as a first detection plane, and one or more detection planes adjacent to the first detection plane are defined as second detection planes, wherein a distance between the trackable element of the first detection plane and an adjacent one of the second detection planes is fixed, and wherein an angle sensor is arranged therebetween and configured to sense an angle between the first detection plane and the adjacent one of the second detection planes.

3. The plane calibration tool of claim 2, wherein the plane calibration tool includes three or more detection planes rotatably connected in sequence, and wherein a length of at least a middle one of the detection planes is adjustable.

4. The plane calibration tool of claim 2, wherein the plane calibration tool includes at least one third detection plane, and the third detection plane has a first side and a second side opposite to the first side, wherein the first side of the third detection plane and the first detection plane are spaced apart by at least one second detection plane, wherein an angle sensor is arranged between the third detection plane and one of the detection planes adjacent to the first side of the third detection plane, and wherein a displacement sensor is arranged on the one of the detection plane adjacent to the first side of the third detection plane, and the displacement sensor is configured to sense a displacement of the third detection plane with respect to another one of the detection planes located at the first side and indirectly adjacent to the third detection plane.

5. A plane calibration tool, comprising at least one detection plane and at least one trackable element, wherein the trackable element is arranged on at least one of the detection planes and the trackable element is fixed in position with respect to the detection plane, and wherein the detection plane is configured to be placed on a current osteotomy plane, and the trackable element is configured for position tracking, wherein the plan calibration tool includes two or more detection planes rotatably connected in sequence, wherein at least one of the detection planes is provided with the trackable element and is defined as a first detection plane, and one or more detection planes adjacent to the first detection plane are defined as second detection planes, wherein the distance between the trackable element of the first detection plane and an adjacent one of the second detection planes is adjustable, and wherein a displacement sensor 1s provided on the first detection plane, and the displacement sensor is configured to sense a displacement of the second detection plane relative to the trackable element.

6. The plane calibration tool of claim 5, wherein the plane calibration tool includes at least one third detection plane, and the third detection plane has a first side and a second side opposite to the first side, wherein the first side of the third detection plane and the first detection plane are spaced apart by at least one second detection plane, wherein an angle sensor is arranged between the third detection plane and one of the detection planes adjacent to the first side of the third detection plane, and wherein a displacement sensor is arranged on the one of the detection plane adjacent to the first side of the third detection plane, and the displacement sensor is configured to sense a displacement of the third detection plane with respect to another one of the detection planes located at the first side and indirectly adjacent to the third detection plane.

* * * * *